United States Patent [19]
Corey

[11] Patent Number: 5,328,850
[45] Date of Patent: * Jul. 12, 1994

[54] MEROCYANINE PROTEIN ERROR INDICATORS

[75] Inventor: Paul F. Corey, Elkhart, Ind.

[73] Assignee: Miles Inc., Elkhart, Ind.

[*] Notice: The portion of the term of this patent subsequent to Jan. 18, 2011 has been disclaimed.

[21] Appl. No.: 989,716

[22] Filed: Dec. 14, 1992

Related U.S. Application Data

[62] Division of Ser. No. 710,955, Jun. 6, 1991, Pat. No. 5,264,589.

[51] Int. Cl.$^5$ ............................................. G01N 33/00
[52] U.S. Cl. ...................................... 436/86; 422/56; 422/57; 436/169; 436/810
[58] Field of Search ................................. 422/55-57; 436/169-170, 86, 810; 252/408

[56] References Cited

U.S. PATENT DOCUMENTS

| | | | |
|---|---|---|---|
| 4,366,241 | 12/1982 | Tom et al. | 422/56 |
| 4,568,647 | 2/1986 | Sanford | 436/88 |
| 4,587,102 | 5/1986 | Nagatomo et al. | 422/56 |
| 4,774,192 | 9/1988 | Terminiello | 422/56 |

OTHER PUBLICATIONS

Easton et al., "Merocyanine 540 as a Fluoroscent Probe of Membranes: Staining of Electrically Excitable Cells" Cell, vol. 13, 475-486, Mar. 1978.

*Primary Examiner*—Lyle A. Alexander
*Attorney, Agent, or Firm*—Roger N. Coe

[57] ABSTRACT

The present test device provides a merocyanine protein error indicator compound. Merocyanine compounds are a new class of protein error indicators, providing an analytical tool useful in the detection of protein in a sample.

15 Claims, 3 Drawing Sheets

MEROCYANINE PROTEIN ERROR INDICATORS

This is a division of application Ser. No. 710,955, filed on Jun. 6, 1991, now U.S. Pat. No. 5,269,589.

BACKGROUND OF THE INVENTION

A. Field Of The Invention

The present invention is related generally to the detection of protein; and more particularly, to a novel class of protein error indicators.

B. Description Of The Background Art

The detection of protein is important in the diagnosis of disease, in medical research and in industry. Several methods exist for the detection of protein in a sample. With the exception of the methodologies using protein error indicators, all of the protein detection techniques are multi-step processes, often requiring highly complex equipment and several hours to complete.

One technique commonly used to measure protein in a sample is the Biuret method. According to this method, the sample is first acidified to precipitate any protein in the sample. The precipitated protein is then re-solubilized in a moderately alkaline medium and treated with a solution containing cupric ions. The peptide bonds of the protein and the cupric ion react to form a colored chelate. The absorbance of the treated solution is then determined using a spectrophotometer. From this data, the amount of protein in the sample is estimated using calibrated spectrophotometric absorbance curves. This method generally takes form 1 to 3 hours to perform.

A variation of the Biuret method is the Lowry method. According to the Lowry method, after the precipitated protein is re-solubilized, a phosphotungstomolybdic acid reagent is added to the solution under alkaline conditions to oxidize any phenolic compounds in the solution. Inasmuch as substantially all proteins contain some phenolic compounds, e.g., tyrosine, this technique is capable of measuring protein in a sample. The absorbance of the treated solution is then measured with a spectrophotometer. Using calibrated spectrophotometer curves, the measured absorbance is thereafter used to estimate the amount of protein in the sample. A number of buffers and other compounds, however, containing amine groups, e.g., TRIS, glycine and amide buffers, interfere with the test.

Another method used to determine the presence of protein in a sample is measuring turbidity following sample acidification. According to the method, the turbidity of the sample is measured using a spectrophotometer following the addition of a protein precipitating agent, generally an acidifying agent, to the sample. The calculated turbidity of the sample is compared to spectrophotometeric standard curves to determine the presence of protein in the sample. Common precipitating agents used in this method include sulfosalicylic acid, trichloracetic acid and tannic acid.

Methodologies using protein error indicators are widely used to determine the presence of protein in a sample. Methods using protein error indicators are inexpensive, fast, simple and convenient. Phenolsulfonephthalein compounds, such as bromophenol blue, bromocresol green and coosmassie blue, are, perhaps, the most widely used protein error indicators. Methodologies using protein error indicators often involve reagent strips which are impregnated with the protein error indicator. According to these methods, the reagent test strip is contacted with a small quantity of the sample. If protein is present in the sample, the test strip will indicate this by simply changing color. The color observed may vary depending on the concentration of protein in the sample. This variable color change is used to quantify the protein in the sample. Reagent strips of the above-type require a minimum of training to use correctly. These reagent test strips provide an accurate, convenient, and rapid vehicle for the on-the-spot determination of protein. Test papers such as these are widely used by technicians in industry, research and clinical laboratories.

In more detail, protein error indicators are pH indicators including an ionizable group which has a pKa value that is displaced by the presence of protein. In the case of the phenolsulfonephthaleins, the ionizable group is a phenolic hydroxyl. The release of the proton from the phenolic hydroxyl causes the observable color change which is indicative of protein in the sample being tested. Protein error indicators which are generally considered useful for the analytical determination of protein in a sample are described in U.S. Pat. No. 4,013,416.

SUMMARY OF THE INVENTION

The present invention provides a merocyanine protein error indicator. Merocyanine protein error indicators are a new class of protein error indicators. Until the present invention, merocyanine dyes were unknown as protein error indicators. Merocyanine protein error indicators are useful for the detection of protein. The merocyanine protein error indicators of the invention are:

Q is —Cl, —Br, or —I;

m is an integer from 1 to 6;

R is S, Se, O, or $C(C_nH_{2n+1})_2$, wherein n is an integer from 1 to 6; and T is $-SO_3^\ominus$ or —H. In accordance with one embodiment of the invention m is 3 or 4; R is $C(CH_3)_2$; and T is $-SO_3^\ominus$.

Another and important aspect of the present invention provides an analytical reagent strip including a merocyanine protein error indicator for the detection of protein in liquid samples.

Still another aspect of the present invention is directed to a method for the detection of protein in a liquid sample. The method comprising the step of wetting an analytical reagent strip with the liquid sample. The test strip is composed of an absorbent carrier impregnated with at least one of the merocyanine protein error indicators described above. The test strip is then observed to detect any color change. A color change is indicative of protein in the liquid sample.

DESCRIPTION OF THE PREFERRED EMBODIMENTS

The present invention is directed to the discovery of a new class of compounds which are useful as protein error indicators. In accordance with one aspect of the invention, it has been discovered that the merocyanine compounds of the invention react with protein resulting in an observable color change in the merocyanine compound. In accordance with another aspect of the invention, it has been discovered that analytical reagent strips for the determination of protein in fluids can be obtained by impregnating an absorbent paper test strip with the novel protein error indicators of the present invention. In accordance with a further aspect of the invention, it has been discovered that the novel protein error indicators of the present invention are useful in aqueous liquid assays. This is particularly advantageous since prior art protein error indicators, such as bromophenol blue, require organic solvents, which can react adversely with the protein in the sample being tested. The protein error of the invention also have pKa values above 3.5. This is advantageous since a wide variety of buffers can be used in constructing a liquid or dip-stick reagent including the inventive indicators.

The below-described novel protein error indicators are orange, and on contact with a sample containing protein become strongly colored pink. The intensity of the color reflecting the concentration of protein in the sample. The pink color produced is clearly distinct from the orange of a negative test. The protein error indicators of the invention positively detect a range of from about 15 to about 500 mg/dl of protein in a sample.

With reference to the observable color change from orange to pink, tests strips prepared in accordance with the present invention are a diagnostic aid for the detection of protein in biological fluids by producing a different and distinct color in the presence of protein which is clearly distinguishable from the orange of a negative test. This is distinguishable from other test strips which change slightly from one shade of a color to another in the presence of albumin, e.g., yellow to yellow-green. The characteristic of orange for a negative test, and pink in a positive test is seen as a significant departure from previous methods and indicators used to detect protein in liquid samples. More specifically, the invention provides clinicians with a reliable method for detecting protein in a sample. The change from orange to pink simplifies the interpretation of the results. This will result in less misinterpretation, and accordingly, lower costs for the user.

The merocyanine protein error indicators of the present invention are the compound:

wherein: Q is —Cl, —Br, or —I; m is an integer from 1 to 6; R is S, O, Se or C($C_nH_{2n+1}$)$_2$, wherein n is an integer from 1 to 6; and where T is —SO$_3$, $\ominus$ or —H.

More preferably, Q is —Br or —I; m is an integer from 2 to 4; R is C(CH$_3$)$_2$; and T is —SO$_3\ominus$. Most preferably, Q is —I; and m is 3.

It should be understood that the present invention describes the first use of the merocyanine class of chromogens as protein error indicators and, accordingly, encompass a wide variety of substituted derivatives. It will be evident that the aromatic rings in the formula can bear a variety of substituent groups without departing from the scope of the present invention. Such substituent groups are limited only by the ability of one of ordinary skill in the art to prepare stable compounds which have the protein error indicator properties of the present invention, and include such groups as unsubstituted and substituted alkyl, unsubstituted and substituted aryl, alkoxy, aryloxy, halo (e.g., fluoro, chloro, bromo), nitro and substituted amino such as dialkylamino.

In the context of the present invention, "alkyl" is intended to include linear and branched forms of unsubstituted hydrocarbon residues of the general formula —$C_nH_{2n+1}$, preferably of the "lower alkyl" aliphatic type wherein n is 6 or less, such as methyl, ethyl, n-propyl, iso-propyl, n-butyl, iso-butyl, tert-butyl, n-hexyl, and the like, as well as substituted forms thereof.

Further, in the context of the present invention "aryl" is intended to include organic residues derived from an aromatic hydrocarbon ring or ring system by removal of a hydrogen atom, and include the unsubstituted hydrocarbon ring residues such as phenyl and naphthyl, and substituted forms thereof. For purposes of the present invention, aryl residues include those bearing one or more same or different functional groups or substituents which can be selected by one skilled in the art to provide the merocyanine protein error indicator compounds of the present invention.

More particularly, where "aryl" and "alkyl" are substituted, such substitution is intended to include such groups or substituents when mono- or polysubstituted with functional groups which do not substantially detract from the useful features of the present compounds. Such functional groups include chemical groups which may be introduced synthetically and result in the stable and useful merocyanine protein error indicator compounds of the present invention. Examples of such functional groups include, but are not intended to be limited to, halo (e.g, fluoro, chloro, bromo), substituted amino such as dialkylamino, nitro, alkoxy, aryloxy, alkyl, and aryl.

Illustrative merocyanine protein error indicators of the inventions include: 1-(ω-sulfopropyl)-2-(4'hydroxy-3',5'-dibromostyryl)-3,3-dimethylindoleninium betaine; 1-(Ωw-sulfobutyl)-2-(4'-hydroxy-3',5'-diiodostyryl)benzothiazolium betaine; 1-(w-sulfoethyl)-2-(4'-hydroxy-3',5'-diiodostyryl)-3,3-dimethylindoleninium betaine; 1-(Ω-sulfopropyl)-2-(4'-hydroxy-3'-5'-diiodostyryl)-3,3-dimethylindoleninium betaine; 1-(ω-sulfobutyl)-2-(4'-hydroxy-3',5'-diiodostyryl)-3,3-dimethylindoleninium betaine; and 1-(n-butyl)-2-(4'-hydroxy-3',5'-diiodostyryl)-3,3-dimethylindoleninium iodide. Detailed protocols for preparing the merocyanine protein error indicators listed above are set forth in the examples.

FIGS. 1–6 generally illustrates the synthesis of several merocyanine protein indicator compounds of the present invention. The chemistry is straight forward and generally involves the coupling of an aromatic hydroxyaldehyde with a heterocyclic quarternary salt under basic reaction conditions. The merocyanine protein error indicators of the invention are water soluble. This is advantageous since these indicators can be added directly to aqueous systems to detect protein, e.g., urine, blood, serum, aqueous gels (electrophoretic gels), aqueous solutions. The general procedures used in the preparing the merocyanine protein error indicators are illustrated in FIGS. 1–6, and are discussed in detail in the examples below.

One aspect of the present invention is directed to an analytical test strip for the detection of protein in a liquid sample or gel comprising an absorbent carrier impregnated with one of the merocyanine protein error indicator compounds described above. The absorbent carrier of the test strip is preferably a filter paper. Other materials useful as the absorbent carrier include felt, porous ceramic strips, and woven or matted glass fibers described in U.S. Pat. No. 3,846,247. Also suggested are the use of wood, cloth, sponge material and argillaceous substances described in U.S. Pat. No. 3,552,928). Alternatively, the absorbent carrier can be non-porous, such as various polymeric films, glass and the like. All such absorbent carrier materials are feasible for use in the present invention, as are others. It has been found, however, that filter paper is especially suitable.

The absorbent strip is preferably impregnated with a buffer. Any buffer system which can be adjusted to a pH of from about 1.5 to about 4.5 is useful in the practice of the present invention. Preferably, the buffer system is adjusted to a pH of from about 2.0 to about 4.0, and most preferably from about 3.5. According to the method, the analytical test strip is contacted by the liquid sample or gel sample. The strip is then observed for a color change. A color change being indicative of protein in the sample.

The following Examples are presented to describe preferred embodiments and utilities of the present invention and are not meant to limit the present invention unless otherwise stated in the claims appended hereto.

EXAMPLES

Example 1

1-(ω-sulfopropyl]-2-(4'-hydroxy-3', 5'-dibromostyryl)-3,3-dimethylindoleninium betaine A solution of 3,5-dibromo-4-hydroxybenzaldehyde (Lancaster Synthesis, Ltd., Windham, N.H. USA) (2.0 g, 7.14 mmole), 1-(ω-sulfopropyl)-2,3,3-trimethylindoleninium betaine (Belg. 726,639; CA 73: P82538a) (2.0 g, 7.11 mmole) and piperidine (0.4 ml) in EtOH (30 ml) was maintained under an inert gas atmosphere. The solution was refluxed for 50 minutes and cooled in an ice bath. The reaction mixture was evaporated to dryness in vacuo, and taken up in a minimum of methanol (MeOH). The solution was thereafter chromatographed on silica gel (600 grams) using MeOH/CHCl$_3$ (1:4 v/v) development. Fractions containing the major purple product band were pooled and acidified with excess HCl in 2-propanol (i-PrOH) to produce the color change from purple to golden yellow. The solution was evaporated to dryness in vacuo. The residue was taken up in hot EtOH (ca. 25 ml) and crystallized upon cooling. The solids that separated were collected by filtration, washed with ice-cold EtOH/hexane (3:1 v/v), and vacuum dried to give the analytically pure compound 1-(ω-sulfopropyl)-2-(4'-hydroxy-3',5'-dibromostyryl)-3,3-dimethylindoleninium betaine (0.96 g, 25%) as golden yellow crystals. The compound had no distinct melting point, but darkened at temperatures above 200°

Figure 1:
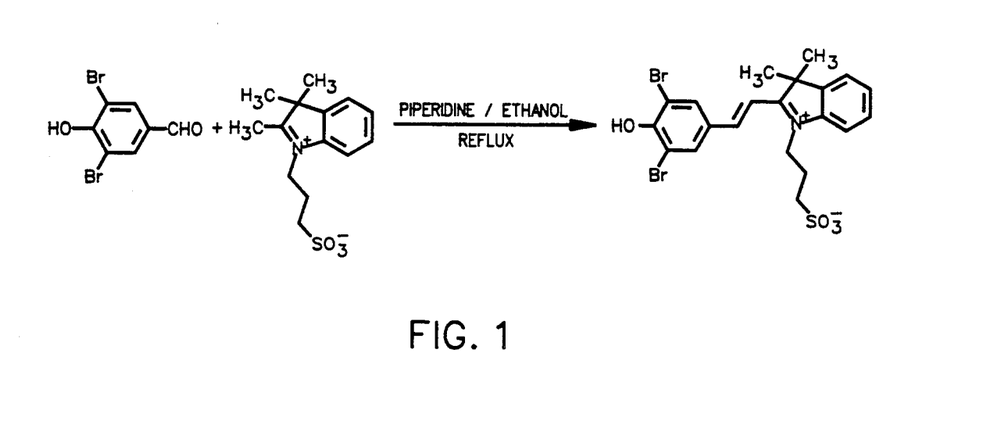
FIGS. 1 to 6 are procedures for the synthesis of merocyanine protein error indicators.
Figure 2:
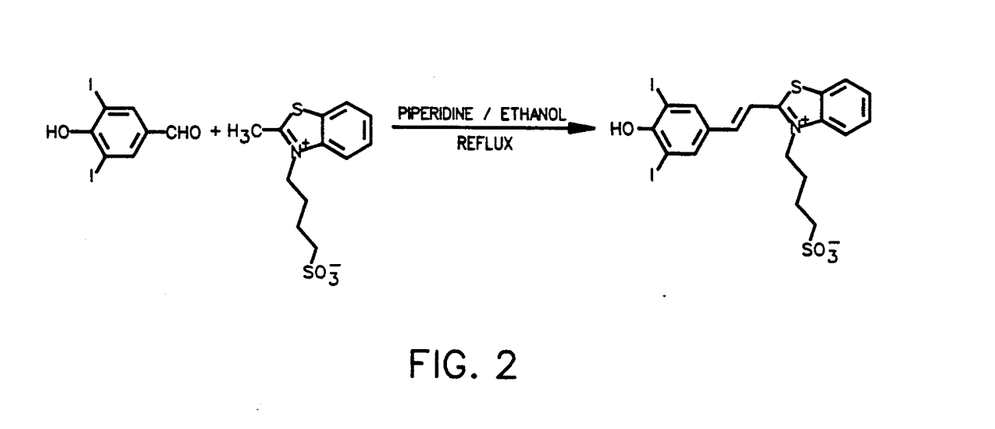
Figure 3:
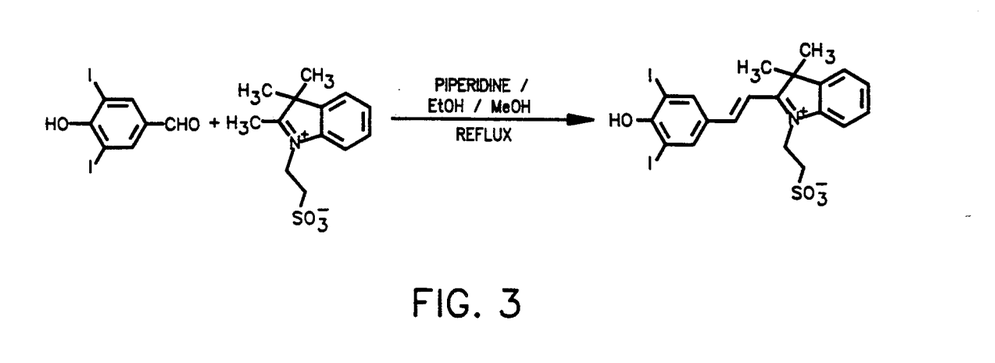

C. The above-described method for preparing the compound is generally illustrated in FIG. 1. Spectroscopic data identifying the compound are set forth below in Table 1.

Table 1

IR (KBr) cm$^{-1}$3438, 3055, 1606, 1577, 1519, 1475, 1406, 1372, 1305, 1277, 1212, 1173, 1124, 739.

$^1$H NMR (DMSO-d$^6$) δ8.58 (s, 2H), 8.29 (d, J=16.0 Hz, 1H), 7.97 (d, J=7.7 Hz, 1H), 7.84 (d of d, J$_1$=2.0 Hz and J$_2$=6.6 Hz, 1H), 7.67 (d, J=16 Hz, 1H), 7.54–7.64 (m, 2H), 4.81 (t, J=7.6 Hz, 2H), 3.77 (v. br. s, 1H), 2.63 (t, J=6.6 Hz, 2H), 2.10–2.22 (m, 2H), 1.76 (s, 6H).

$^{13}$C NMR(DMSO-d$^6$) ppm 181.6, 155.6, 151.3, 143.8, 140.9, 135.1, 129.2, 129.1, 128.7, 123.0, 115.2, 112.5, 111.6, 52.2, 47.3, 45.5, 25.6, 24.8 (3 coincident bands).

Anal. Calcd for C$_{21}$H$_{21}$Br$_2$NO$_4$S.½EtOH: C, 46.65; H,4.27; N,: 2.47; Found: C, 46.48; H, 4.50; N, 2.33.

Example 2

1-(ω-sulfobutyl)-2-(4'-hydroxy-3',5'-diiodostyryl)-benzothiazolium betaine

A mixture of 3,5-diiodo-4-hydroxybenzaldehyde (Lancaster Syntheses, Ltd., Windham, N.H., USA) (3.74 g, 10 mmole), 3-(ω-sulfobutyl)-2-methylbenzothiazolium betaine (Brit. 742, 112; CA 50: Pl1149c) (3.71 g, 13 mmole) and piperidine (0.8 ml) in EtOH (30 ml) was maintained under an inert gas atmosphere. The solution was refluxed for one hour then cooled to ambient temperature. The reaction mixture was acidified with sufficient 1.93 M hydrochloric acid in i-PrOH to effect a color change from purple to yellow whereupon solids separated from the solution. The solids were collected by filtration, washed with EtOH and dried. The solids were then dissolved in warm (55° C.) EtOH/MeOH/H$_2$O (3:2:1 v/v/v) (300 ml) containing 2 M aqueous sodium hydroxide (5.2 ml), filtered through Celite (Johns-Manville Corp., Denver, Colo. USA) and precipitated by the addition of 3M aqueous hydrochloric acid (6 ml). After cooling in an ice bath, the solids were collected by filtration, washed with EtOH and dried in vacuo. The solids were then boiled in acetic acid (HOAc) (600ml), filtered and dried in vacuo at 115° C. to afford the analytically pure compound 1-(ω-sulfobutyl)-2-(4'-hydroxy-3',5'-diiodostyryl)benzothiazolium betaine (5.10 g, 79%) as a yellow powder. The above-described method for preparing the compound is generally illustrated FIG. 2. Spectroscopic data identifying the compound are set forth below in Table 2.

Table 2

IR (KBr) cm$^{-1}$3436, 1608, 1572, 1529, 1497, 1458, 1396, 1318, 1267, 1208, 1038.

$^1$H NMR (DMSO-d$_6$) δ8.55 (s, 1H), 8.30–8.50 (m, 3H), 7.92–8.16 (m, 3H), 7.73–7.88 (m, 2h), 4.95 (br. t, J=7.5Hz, 2H), 2.53 (t, J=7.1 Hz, 2H), 1.98 (br. m, 2H), 1.81 (q, J=7.0Hz, 2H).

$^{13}$C NMR (DMSO-d$^6$) ppm 171.4, 159.1, 148.1, 146.1, 141.0, 140.6, 131.5 129.2, 128.0, 123.9,116.7, 112.2, 86.4, 50.0, 48.8, 27.2, 21.9 (2 coincident bands).

Analysis calculated for C$_{19}$H$_{17}$I$_2$NS$_2$O$_4$: C, 35.58; H, 2.67; N, 2.18; Found: C, 35.52; H, 2.75; N, 2.06.

Example 3

1-(ω-sulfoethyl)-2-(4'-hydroxy-3', 5'-diiodostyryl)-3,3-dimethylindoleninium betaine A mixture of 3,5-diiodo-4-hydroxybenzaldehyde (3.73 g, 10 mmole), 1-(ω-sulfoethyl)-2,3,3-trimethylindoleninium bromide (U.S. Pat. No. 2,503,776; CA 44: P5738i) (6.61 g; 19 mmole) and piperidine (2.0ml) in EtOH/MeOH (2:1 v/v) (60 ml) was maintained under an inert gas atmosphere. The solution was refluxed for 4 hours, cooled to an ambient temperature, and evaporated to dryness in vacuo leaving a brown residue. The brown residue was taken up in MeOH (2–3 ml). This solution was treated with triethylamine (NEt$_3$) (2 ml) and chromatographed on silica gel using MeOH/CHC$_3$ (1:4 v/v) development. Fractions containing the purple product band were pooled and evaporated to dryness in vacuo. This crude product was taken up in EtOH (10 ml), acidified with sufficient 1.93 M HCl in i-PrOH to effect a color change from purple to yellow. This solution was evaporated to dryness. The residue was then taken up in EtOH/hexane (3:1 v/v), and refrigerated until the solution crystallized. The crystalline solids that separated were collected by filtration. These solids were washed with ice-cold EtOH and then EtOH/hexane. The remaining solids were vacuum dried to give the compound 1-(e-sulfoethyl)-2-(4'-hydroxy-3',5'-diiodostyryl)-3,3-dimethylindoleninium betaine (0.80 g; 12.8%). Recrystallization from EtOH/HOAc afforded the analytically pure compound as a dark reddish-brown powder. The above-described method for preparing the compound is generally illustrated as reaction in FIG. 3. Spectroscopic data identifying the compound are set forth below in Table 3.

Table 3

IR (KBr) cm$^{-1}$ 3444, 2992, 1608, 1574, 1530, 1469, 1399, 1371, 1327, 1296, 1282, 1230, 1212, 1178, 1141, 1086, 1033, 964.

$^1$H NMR (DMSO-d$^6$) δ8.58 (s, 2H), 8.18 (d, J=16.3 Hz, 1H), 7.69–7.88 (m, 4H), 7.51–7.62 (m, 2H), 4.82 (t, J=5.7 Hz, 2H), 3.04 (t, J=6.1 Hz, 2H), 1.73 (s, 6H);

$^{13}$C NMR (DMSO-d$_6$)ppm 182.4, 160.0, 149.1, 143.6, 141.4, 140.7, 130.5, 128.8, 122.8, 115.1, 112.9, 87.3, 52.0, 47.7, 43.7, 25.4 (4 coincident bands).

Analysis calculated for C$_{20}$H$_{19}$I$_2$NO$_4$S.½%EtOH: C, 39.02; H, 3.43; N, 2.16; Found: C, 39.25; H, 3.47; N, 2.25.

EXAMPLE 4

Figure 4:
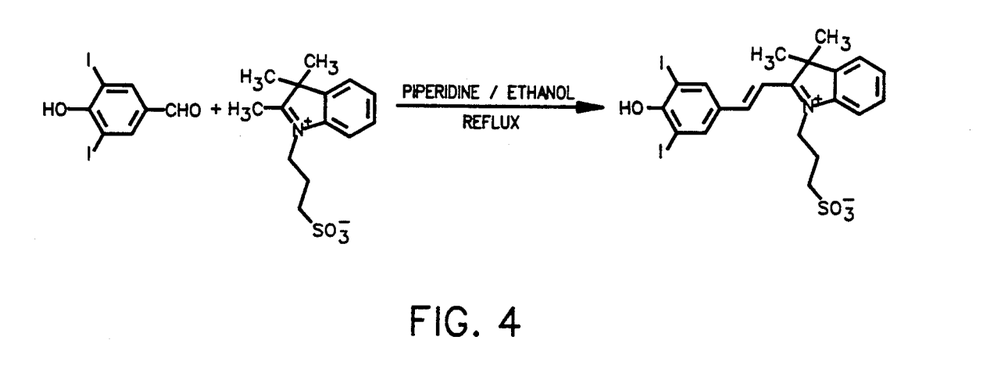
Figure 5:
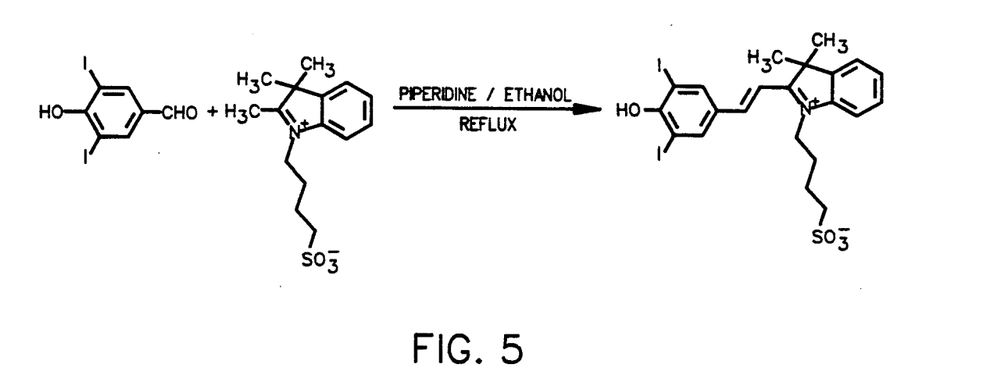
Figure 6:
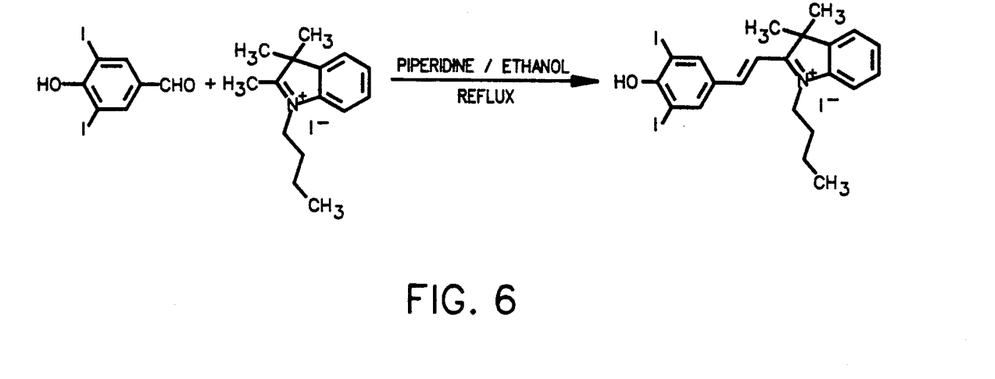

1-(ω-sulfopropyl)-2-(4'-hydroxy-3',5'-diiodostyryl)-3,3-dimethylindoleninium betaine (SPDIB A mixture of 3,5-diiodo-4-hydroxybenzaldehyde (3.73 g, 10 mmole), 1-(ω-sulfopropyl)-2,3,3-trimethylindoleninium betaine (3.65 g, 13 mmole) and piperidine (0.8 ml) in EtOH (ca. 50 Ml) was maintained under an inert gas atmosphere. The solution was refluxed for 2.75 hours and then cooled in an ice bath. The solution was acidified with 1.93 M HCl in i-PrOH (5.0 ml). A dark tar separated and was collected by filtration and triturated with boiling HOAc. The combined triturates were evaporated to dryness in vacuo, taken up in HOAc (20 ml) and allowed to crystallize. The solids that separated were collected by filtration, washed with HOAc and vacuum dried to give the compound 1-(ω-sulfopropyl)-2-(4'-hydroxy-3',5'-diiodostyryl)-3,3-dimethylindoleninium betaine (4.37 g, 68%) as an orange powder. The compound was recrystallized from HOAc to afford the analytically pure compound. The above-described method for preparing the compound is generally illustrated in FIG. 4. Spectroscopic data identifying the compound are set forth below in Table 4.

Table 4

IR (KBr) cm$^{-1}$ 1604, 1572, 1526, 1468, 1402, 1376, 1274, 1214, 1173, 766, 722.

$^1$H NMR (DMSO-d$^6$) δ8.71 (s, 2H), 8.21 (d, J=15.5 Hz, 1H), 7 . 92 (d, J=7.2 Hz, 1H), 7.81 (d, J=6.6 Hz, 1H), 7.50–7.65 (m, 3H), 4.72–4.82 (v. br. m, 2H), 3.57 (v.br. s, 1H), 2.61 (t, J=6.5 Hz, 2H), 2.07–2.20 (v. br. m, 2H) 1.76 (s, 6H).

$^{13}$C NMR (DMSO-d$^6$) ppm 181.3, 160.6, 151.1, 143.7, 142.0, 140.9, 130.0, 129.1, 122.9, 115.0, 110.7, 87.4, 52.0, 47.3, 45.4, 25.7, 24.7 (4 coincident bands).

Analysis calculated for C$_{21}$H$_{21}$I$_2$NO$_4$S.½H$_2$O: C,39.02; H, 3.43; N, 2.17. C,39.01; H, 3.46; N, 1.94. Found:

Example 5.

1-(ω-sulfobutyl)-2-(4'-hydroxy-3', 5'-diiodostyryl)-3,3-dimethylindoleninium betaine A mixture of 3,5-diiodo-4-hydroxybenzaldehyde (1.87 g, 5 mmole), 1-(ω-sulfobutyl)-2,3,3-trimethylindoleninium betaine (R. B. Mujumdar et al., *Cytometry* 10, 11–9 (1989)) (2.36 g, 8 mmole) and piperidine (0.4 ml) in EtOH (35 ml) was maintained under an inert gas atmosphere. The solution was refluxed for 2.5 hours and then cooled to an ambient temperature. The reaction mixture was acidified with an excess of 1.93 M HCl in i-PrOH, and evaporated to dryness in vacuo, leaving a residue. The residue was taken up in EtOH (10ml). On standing in a refrigerator, solids separated from the mixture. The solids were collected by filtration, washed with ice-cold EtOH/hexane (3:1 v/v), and vacuum dried to afford an orange solid (3.36 g). The crude product was taken up in boiling EtOH (ca. 30 ml) and immediately reprecipitated. Additional boiling EtOH was added, (ca. 220 mL) but the solid did not redissolve. After cooling in ice the solids were collected by filtration, washed with EtOH and vacuum dried to afford the analytically pure compound 1-(ω-sulfobutyl)-2-(4'-hydroxy-3',5'-diiodostyryl)-3,3-dimethylindoleninium betaine (1.54 g, 47%) as an orange powder. The above-described method for preparing the compound is generally illustrated FIG. 5. Spectroscopy data identifying the compound is set forth below in Table 5.

Table 5

IR (KBr) cm$^{-1}$: 2977, 1605, 1572, 1525, 1469, 1401, 1372, 1308, 1271, 1214, 1182, 1120, 1034, 769, 714.

$^1$H NMR (DMSO-d$^6$) δ8.71 (s, 2H), 8.24 (d, J=16.0 Hz, 1H), 7.90–7.97 (m, 1H), 7.81–7.87 (m, 1H), 7.53–7.64 (m, 3H), 4.68 (t, J=7.2 Hz, 2H), 2.45–2.55 (m, 2H), 1.89–2.00 (m, 2H), 1.75–1.83 (m, 2H), 1.76 (s, 6H).

$^{13}$C NMR (DMSO-d$^6$)ppm 181.3, 160.5, 151.1, 143.7, 141.9, 140.8, 130.0, 129.0, 122.9, 115.2, 110.7, 87.3, 52.0, 50.3, 46.2, 27.2, 25.8, 22.3 (4 coincident bands).

Analysis calculated for C$_{22}$H$_{23}$I$_2$NO$_4$S: C, 40.57; H, 3.56; N, 2.15; Found: C, 40.59; H, 3.50; N,1.99.

Example 6

1-(n-butyl)-2-(4'-hydroxy-3',5'-diiodostyryl)-3,3-dimethylindoleninium iodide.

A mixture of 3,5-diiodo-4-hydroxybenzaldehyde (3.73, 10 mmole), 1-(n-butyl)-2,3,3-trimethylindoleninium iodide (D. P. Maisuradze et al., Soobschch. Akad. Nauk Gruz. SSR 50, 77–82 (1968); CA 69: 106526r) (4.46 g, 13 mmole) and piperidine (0.8 ml) in EtOH (40 ml) was maintained under an inert gas atmosphere. The solution was refluxed for 1 hour, and cooled to an ambient temperature. The solution was evaporated to dryness in vacuo, leaving a residue. The residue was taken up in EtOH (10 ml) and treated with 1.93 M HCl in i-PrOH (3.0 ml). The solution was thereafter again evaporated to dryness in vacuo, leaving a residue. The residue was taken up in EtOH (4 ml). The solution was refrigerated and crystals spontaneously formed. The crystalline solids that separated were collected by filtration, washed with ice-cold EtOH and vacuum dried to give crude 1-(n-Butyl)-2-(4'-hydroxy-3',5'-diiodostyryl)-3,3-dimethylindoleninium iodide (4.90 g, 80.7%). The crude compound was taken up in hot EtOH (60 ml), filtered through paper and concentrated in vacuo to about 30 ml. The solution was allowed to crystallize. The crystalline solids that separated were collected, washed and dried as above to afford the analytically pure compound 1-(n-butyl)-2-(4'-hydroxy-3',5'-diiodostyryl)-3,3-dimethylindoleninium iodide (3.90 g, 56%) as a bright orange powder. The above-described method for preparing the compound is generally illustrated as reaction F of FIG. 1. Spectroscopic data identifying the compound is set forth below in Table 6.

TABLE 6

IR (KBr) cm$^{-1}$3361, 2979, 1605, 1574, 1530, 1463, 1402, 1372, 1320, 1250, 1213, 1198, 1136.

$^1$H NMR (DMSO-d$^6$) δ8.63 (s, 2H), 8.23 (d, J=15.9 Hz, 1H), 7.39–7.87 (m, 6H), 4.65 (t, J=7.0, 2H), 1.73–1.85 (m, 2H), 1.76 (s, 6H), 1.34–1.48 (m, 2H), 0.93 (t, J=7.3 Hz, 3H).

$^3$C NMR (DMSO-d$^6$) ppm 181.2, 160.7, 150.9, 143.7, 141.7, 140.7, 129.8, 129.0, 123.0, 115.0, 110.4, 87.7, 52.0, 46.1, 30.4, 25.8, 19.2, 13.7 (4 coincident bands).

Analysis calculated for $C_{22}H_{24}I_3NO \cdot EtOH$: C, 38.68; H, 4.06; N 1.89; Found: C, 38.55;H,3.96;N,1.91;

Example 7

Performance In Assay For Human Serum Albumin

The utility of the merocyanine protein error indicator compounds of the present invention in a liquid assay for the determination of protein levels in a liquid test sample is illustrated in 10 Table 7 below. A solution of the compounds, in 200 mM–250 mM Na$^+$ or K$^+$ citrate buffer at a pH at least 0.5 unit below the pK$_a$ of the compound, was prepared and its absorbance measured at the listed wavelength below. The solution was then treated with sufficient human serum albumin to make the albumin concentration 100 mg/dl and the absorbance was measured again. The reported increase in absorbance (Δ abs) is proportional to the amount of albumin present, and is indicative of the relative sensitivity of the dye for measuring protein.

TABLE 7

| COMPD. No. | COMPD. pKa. | COMPD. CONC. (M) | ASSAY pH | ASSAY λ (nm) | ΔABS |
|---|---|---|---|---|---|
| A | 3.59 | 1.0 × 10$^{-5}$ | 3.0 | 522 | 0.156 |
| B | 4.35 | 2.5 × 10$^{-5}$ | 3.5 | 506 | 0.027 |
| C | 3.65 | 1.5 × 10$^{-5}$ | 3.0 | 543 | 0.255 |
| D | 3.65 | 2.0 × 10$^{-5}$ | 3.0 | 541 | 0.402 |

TABLE 7-continued

| COMPD. No. | COMPD. pKa. | COMPD. CONC. (M) | ASSAY pH | ASSAY λ (nm) | ΔABS |
|---|---|---|---|---|---|
| E | 3.52 | 1.8 × 10$^{-5}$ | 3.0 | 535 | 0.322 |

Compound A is 1-(ω-sulfopropyl)-2-(4 'hydroxy-3',5'-dibromostyryl)-3,3-dimethylindoleninium betaine Compound B is 1-(ω-sulfobutyl)-2-(4'-hydroxy-3',5'-diiodostyryl)-benzothiazolium betaine Compound C is 1-(ω-sulfoethyl)-2-(4'-hydroxy-3',5'-diiodostyryl)-3,3-dimethylindoleninium betaine Compound D 1-(ω-sulfopropyl)-2-(4'-hydroxy-3'-5'-diiodostyryl)-3,3-dimethylindoleninium betaine Compound E is 1-(ω-sulfobutyl)-2-(4'-hydroxy-3',5'-diiodostyryl)-3,3-dimethylindoleninium betaine.

Example 8

Reagent Strap Preparation

One method for the preparation of the analytical protein reagent strips discussed herein is shown below. The method described is a continuous method for mass producing protein reagent test strips.

According to the method, a thin absorbent strip of paper is moved through the line at a preferred speed of about four feet per minute. One preferred paper being E & D 237 (Ahlstrom Filtration, Inc., Mount Holley Springs, Pa., U.S.A.). The paper is dipped into a buffered bath, pH 2.5, including the merocyanine protein error indicator SPDIB dissolved in ethanol. According to one preferred method, the bath contains from about 0.03 to about 0.08mM SPDIB, a 0.5 M potassium citrate buffer pH 2.5, and 20% ethanol. The test strip is then passed through a dryer having an air pressure of one inch of water and a temperature of 60° C. at a speed of four feet per minute. The test strips are then cut and packaged.

Example 9

The Dose Response of Reagent Strips Including SPDIB

A buffered liquid sample (50 mM potassium citrate, pH 2.5) which was shown by immunoassay to be devoid of albumin, was spiked to various clinically significant levels with Pentex® human serum albumin (HSA) (Miles, Inc., Elkhart, Ind.). Using a Clinitek 200®Instrument (Miles, Inc., Elkhart, Ind.) protein measurements were made using analytical test strips including 0.3 mM SPDIB.

Figure 7:
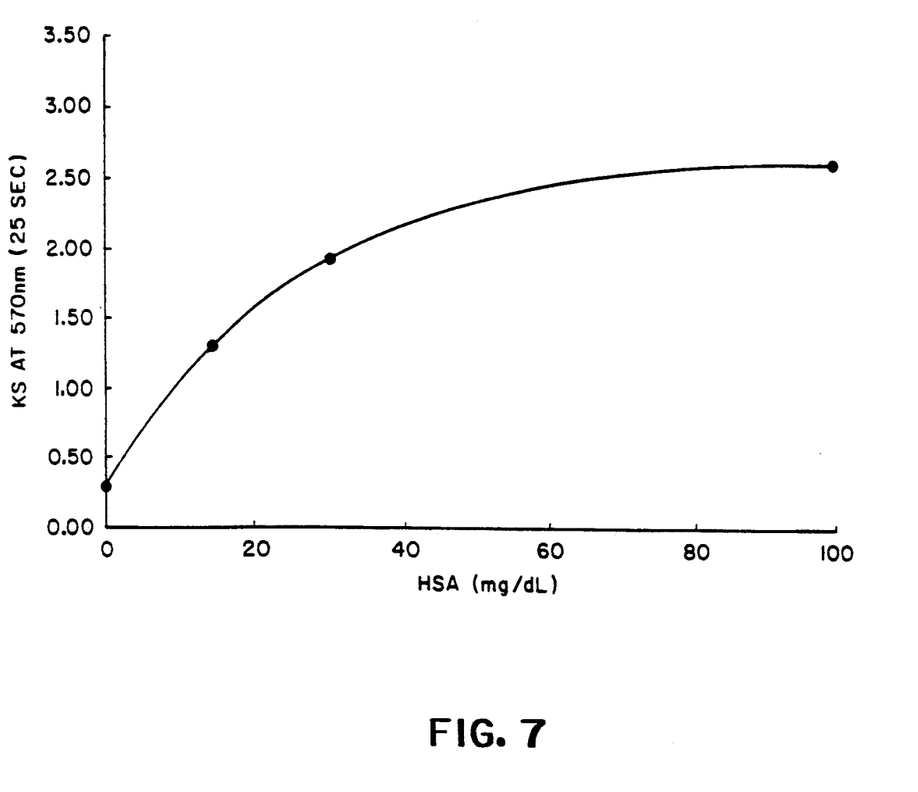
FIG. 7 illustrates the dose response curve to albumin of an analytical test strip impregnated with 0.3 mM SPDIB (1-(ω-sulfopropyl)-2-(4'-hydroxy-3'-5'-diiodostyryl)-3,3-dimethylindoleninium betaine) at pH 2.5.

Resolution was quantitatively expressed in delta K/S between albumin levels, as shown FIG. 7. K/S are calculated from the formula:

$$K/S = \frac{(1 - R)^2}{2R}$$

wherein R is the fraction of reflectance from the test device, K is a constant, and S is the light scattering coefficient of the particular reflecting medium. The above equation is a simplified form of the well-known Kubelka-Munk equation (See Gustav Kortum, "Reflectance Spectroscopy," pp. 106–11, Springer Verlas, New York (1969). K/S was determined at 25 seconds.

The reagent strip described above were analyzed for their response to the different levels of protein. The results of this study are summarized as FIG. 7. As shown in FIG. 7, the strip of the invention was sensitive to a wide range of protein concentrations. Furthermore, a significant resolution between protein levels was seen with the invention.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

I claim:

1. An analytical test strip for the detection of protein in a liquid sample comprising an absorbent carrier impregnated with the merocyanine protein error indicator compound:

wherein:
m is an integer from 1 to 6;
Q is —Br, —I, or Cl;
R is S, Se, O, or $C(C_nH_{2n+1})_2$, wherein:
n is an integer from 1 to 6; and
T is —$SO_3^\ominus$ or —H.

2. The analytical test strip of claim 1 wherein m is the integer 3 or 4; Q is —Br or —H I; R is $C(_nH_{2n+1})_2$, wherein n is an integer from 1 to 3; and T is —$SO_3^\ominus$.

3. The analytical test strip of claim 1 wherein m is the integer 3; and R is $C(CH_3)_2$.

4. A method for the detection of protein in a liquid sample, the method comprising the steps of:
a) wetting an analytical test strip with the liquid sample, the test strip including an absorbent carrier impregnated with the merocyanine protein error indicator compound:

wherein:
m is an integer from 1 to 6;
Q is —Br, —I, or Cl;
R is S, Se, O, or $C(C_nH_{2n+1})_2$, wherein:
n is an integer from 1 to 6; and
T is —$SO_3^\ominus$ or —H; and
b) observing and recording any color change of the test strip, wherein a color change is indicative of protein in the liquid sample.

5. The method of claim 4 wherein the merocyanine protein error indicator compound is further defined as m is the integer 3 or 4; Q is —Br or —I; R is $C(C_nH_{2n+1})_2$, wherein n is an integer from 1 to 3; and T is —$SO_3^\ominus$.

6. The method of claim 4 wherein the merocyanine protein error indicator compound is further defined as m is the integer 3; and R is $C(CH_3)_2$.

7. The method of claim 4 wherein the merocyanine protein error indicator compound is 1-(ω-sulfopropyl)-2-(4'-hydroxy-3'-5'-diiodostyryl)-3,3-dimethylindoleninium betaine.

8. The method of claim 4 wherein the liquid sample is a body fluid.

9. The method of claim 4 wherein the liquid sample is urine.

10. A method for the detection of protein in a sample, the method comprising the steps of:
a) adding to the sample the merocyanine protein error indicator compound:

wherein:
m is an integer from 1 to 6;
Q is —Br, —I, or Cl;
R is S, Se, O, or $C(C_nH_{2n+1})_2$, wherein:
n is an integer from 1 to 6; and
T is —$SO_3^\ominus$ or —H; and
b) observing and recording any color change, wherein a color change is indicative of protein in the sample.

11. The method of claim 10 wherein the merocyanine protein error indicator compound is further defined as m is the integer 3 or 4; Q is —Br or —I; R is $C(C_nH_{2n+1})_2$, wherein n is an integer from 1 to 3; and T is —$SO_3^\ominus$.

12. The method of claim 11 wherein the merocyanine protein error indicator compound is further defined as m is the integer 3; and R is $C(CH_3)_2$.

13. The method of claim 10 wherein the 2 merocyanine protein error indicator compound is 1-(ω-sulfopropyl)-2-(4'-hydroxy-3'-5'-diiodostyryl)-3,3-dimethylindoleninium betaine.

14. The method of claim 10 wherein the sample is an electrophoretic gel.

15. The method of claim 10 wherein the sample is a liquid.

* * * * *

UNITED STATES PATENT AND TRADEMARK OFFICE
CERTIFICATE OF CORRECTION

PATENT NO. : 5,328,850
DATED : July 12, 1994
INVENTOR(S) : Paul F. Corey

It is certified that error appears in the above-identified patent and that said Letters Patent is hereby corrected as shown below:

Col. 11, line 37, delete "Q is - Br or-H1; Ris $C(_nH_{2n+1})2$," and insert -- Q is - Br or -1; R is $C(C_nH_{2n+1})2$, --

Col. 12, line 9 delete "$C(C_nH_{2+1})_2$" and insert -- $C(C_nH_{2n+1})_2$ --

Col. 12, line 53-54, delete "wherein the 2 merocyanine" and insert-- wherein the merocyanine --

Signed and Sealed this

Twenty-sixth Day of August, 1997

Attest:

BRUCE LEHMAN

*Attesting Officer*          *Commissioner of Patents and Trademarks*